United States Patent [19]

Tyle et al.

[11] Patent Number: 5,314,685
[45] Date of Patent: May 24, 1994

[54] ANHYDROUS FORMULATIONS FOR ADMINISTERING LIPOPHILIC AGENTS

[75] Inventors: Praveen Tyle; Kenneth R. Freebern, both of San Diego, Calif.

[73] Assignee: Agouron Pharmaceuticals, Inc., San Diego, Calif.

[21] Appl. No.: 881,085

[22] Filed: May 11, 1992

[51] Int. Cl.⁵ .................... A61K 7/02; A61K 31/74
[52] U.S. Cl. ................................ 424/401; 514/937
[58] Field of Search ............ 424/401, 78.03, 78.05, 424/78.06, 78.07

[56] References Cited

U.S. PATENT DOCUMENTS

| | | | |
|---|---|---|---|
| Re. 32,393 | 4/1987 | Wretlind et al. | 514/219 |
| 2,173,203 | 9/1939 | Harris | 167/91 |
| 4,230,702 | 10/1980 | Eckert et al. | 424/242 |
| 4,284,621 | 8/1981 | Preuss et al. | 424/59 |
| 4,459,404 | 7/1984 | Frickel et al. | 548/253 |
| 4,707,293 | 11/1987 | Ferro | 252/174.17 |
| 4,719,239 | 1/1988 | Muller et al. | 514/785 |
| 4,722,941 | 2/1988 | Eckert et al. | 514/784 |
| 4,731,384 | 3/1988 | Dell et al. | 514/658 |
| 4,760,096 | 7/1988 | Sakai et al. | 514/847 |
| 4,767,751 | 8/1988 | Davis | 514/179 |
| 4,769,360 | 9/1988 | Roelz et al. | 514/588 |
| 4,775,678 | 10/1988 | Su et al. | 514/396 |
| 4,837,213 | 6/1989 | Caron et al. | 514/179 |
| 4,874,605 | 10/1989 | Urban, Jr. et al. | 514/944 |
| 4,883,660 | 11/1989 | Blackman et al. | 424/78 |
| 4,892,888 | 1/1990 | Grollier et al. | 514/132 |
| 4,959,365 | 9/1990 | Francoeur et al. | 514/237.5 |
| 4,970,216 | 11/1990 | Deckner et al. | 514/311 |
| 5,001,156 | 3/1991 | Philippe et al. | 514/555 |
| 5,039,516 | 8/1991 | Goodman et al. | 424/59 |
| 5,059,626 | 10/1991 | Park et al. | 514/658 |
| 5,096,711 | 3/1992 | Dookhith et al. | 424/405 |
| 5,098,606 | 3/1992 | Nakajima et al. | 252/358 |
| 5,104,656 | 4/1992 | Seth et al. | 424/401 |
| 5,106,625 | 4/1992 | Yamamoto et al. | 424/401 |

Primary Examiner—Thurman K. Page
Assistant Examiner—C. Azpuru
Attorney, Agent, or Firm—Finnegan, Henderson, Farabow, Garrett & Dunner

[57] ABSTRACT

Anhydrous formulations useful for administering lipophilic, pharmaceutically active agents to hosts in need of such treatment processes for preparing these formulations, pharmaceutical compositions based upon these formulations, and the use of these formulations to administer lipophilic, pharmaceutically active agents to a host. The lipophilic agent to be administered is solubilized in a hydrophilic vehicle which makes up at least part of the anhydrous formulation. Preferably, the lipophilic agent is present in the hydrophilic vehicle in a supersaturated or near saturated amount. Preferred pharmaceutical compositions based upon the formulations according to the present invention are useful in treating skin dermatoses such as psoriasis.

4 Claims, No Drawings

ANHYDROUS FORMULATIONS FOR ADMINISTERING LIPOPHILIC AGENTS

FIELD OF THE INVENTION

The present invention relates to anhydrous formulations useful for administering lipophilic, pharmaceutically active agents to hosts in need of treatment, processes for preparing these formulations, pharmaceutical compositions based upon these formulations, and the use of these formulations to administer lipophilic, pharmaceutically active agents to a host. The lipophilic agent to be administered is solubilized in a hydrophilic vehicle which makes up at least part of the anhydrous formulation. Preferably, the lipophilic agent is present in the hydrophilic vehicle in a supersaturated or near saturated amount. Preferred pharmaceutical compositions based upon the formulations according to the present invention are useful in treating skin dermatoses such as psoriasis.

BACKGROUND OF THE INVENTION

Various methods are known for administering pharmaceutically active agents to a host in need of treatment. For example, such agents are often administered topically, parenterally, orally, ocularly, or nasally, depending upon the nature of the illness being treated.

The therapeutic activity of a pharmaceutical agent administered in one of these manners is often influenced both by passive availability, namely the ability of the pharmaceutically active agent to be released from the carrier composition used to administer the agent, and by biological availability, namely the agent's ability to pass through a membrane. The lesser of these typically determines the speed of absorption of a pharmaceutically active agent by an organism.

In the case of topical applications, for example, the pharmaceutically active agent must be released from the carrier composition and partition into and penetrate the epidermis of the skin before it can be absorbed and transferred to elicit its pharmacological effects. Generally, passage through the epidermis is the slowest and consequently the rate-determining step. Enhanced passage through the epidermis is often attempted by selecting carrier compositions tailored to the particular pharmaceutically active agent being administered.

Various methods are known for improving the absorbability of poorly absorbable pharmaceutically active agents. For example, absorbability in some cases is improved through a technological treatment of the pharmaceutically active agent, e.g., by means of micronization or complex-formation, or through the addition of solubility improving additives.

These techniques, however, exhibit many disadvantages. For example, these techniques often require the use of special apparatuses or process steps during preparation, and some of these techniques are successful for only a limited number of pharmaceutically active agents. Furthermore, only a limited number and amount of additives may be employed in certain cases due to safety and/or compatibility problems.

There is therefore a need in the art for formulations which provide a high degree of absorption, when applied topically, parenterally or orally, for pharmaceutically active agents which are themselves per se poorly absorbable or highly insoluble.

Furthermore, there is a need in the art for formulations which are optimally effective in delivering lipophilic, pharmaceutically active agents in a solubilized form to a host for treating skin dermatoses such as psoriasis. Psoriasis is a nonmalignant skin disease of abnormal cell proliferation and is among the dermatoses having a poorly understood etiology. Although many antimetabolites are known to be active against psoriasis, many are mutagenic or carcinogenic analogs. Therefore, there is a particular need in the art for non-carcinogenic, pharmaceutically active compounds which are effective in treating psoriasis.

Pharmaceutically active agents effective in treating dermatological conditions are typically incorporated in a suitable oil or water based ointment, lotion or cream vehicle to promote uniform application and effective transdermal absorption. In the past, oil-based vehicles for topical medicaments have suffered several drawbacks. For example, many oil-based vehicles are not water washable and have a tendency to adhere to and stain clothing. Furthermore, the greasy nature of many oil-based compositions served to inhibit the release and subsequent absorption of many topically pharmaceutically active agents.

To overcome the defects described above, several water-based formulations have been developed which are water washable, non-staining, and which provide satisfactory spreadability and adherence while not inhibiting the release of pharmaceutically active agents incorporated therein. These water-based formulations, however, also suffer drawbacks in that they are not suitable for use with pharmaceutically active agents which are water-decomposable or water-insoluble.

SUMMARY OF THE INVENTION

The present invention, which overcomes several of the problems discussed above, relates to anhydrous cream formulations made up of (a) an anhydrous hydrophilic phase comprising at least one hydrophilic vehicle suitable for solubilizing at least one lipophilic, pharmaceutically active agent to be administered to a host in need of treatment, and (b) an oily phase which is partially miscible with the at least one hydrophilic vehicle of the anhydrous hydrophilic phase. The lipophilic, pharmaceutically active agent or agents to be administered to the host in need of treatment are solubilized in the anhydrous hydrophilic phase of the formulations. Preferably, the lipophilic agent is present in the hydrophilic vehicle of the anhydrous hydrophilic phase in a supersaturated or near saturated amount. Preferred pharmaceutical compositions based upon the formulations of the present invention are useful in treating skin dermatoses such as psoriasis.

DETAILED DESCRIPTION OF THE INVENTION

As discussed previously, the present invention relates to anhydrous formulations useful for administering lipophilic, pharmaceutically active agents, in a solubilized form, to hosts in need of treatment, processes for preparing these formulations, pharmaceutical compositions based upon these formulations, and the use of these formulations to administer lipophilic, pharmaceutically active agents to hosts in need of treatment.

The term "pharmaceutically active" as used herein is meant to denote agents which are effective in treating larger mammals, particularly human beings, in treating or preventing diseases and/or body function disorders.

The term "partially miscible" means that the two phases are not completely soluble in each other.

The term "poorly absorbable" is meant to denote agents which, upon being enterally or topically applied in a solid or liquid composition devoid of any dissolution and/or absorbability improving additives, exhibit such a low and/or slow per se absorbability, that by means of enteral or topical administration, a pharmaceutically effective level in the body of larger mammals cannot be reached or can be reached only by administering a dosage much larger than is necessary to achieve a pharmaceutically effective level of the respective agent in the host. Whether the actual per se absorbability of a particular pharmaceutically active agent is sufficient or insufficient, of course, depends upon the chemical and physical properties of the agent, especially the kind and degree of its pharmaceutical activity as well as the desired pharmaceutical effect.

The anhydrous formulations according to the present invention are particularly useful in administering poorly absorbable compounds which demonstrate low in vitro flux in human cadaverous skin when administered alone and thus do not exert the therapeutic effect of interest. By use of the anhydrous formulations according to the present invention, in vitro flux rates in human cadaverous skin can be increased 1-100 fold as compared to conventional dosage forms.

The language "suitable for solubilizing at least one lipophilic, pharmaceutically active agent to be administered to a host in need of treatment" refers to vehicles which promote the release and absorption of a lipophilic, pharmaceutically active agent into the host being treated.

The anhydrous formulations according to the present invention comprise (a) an anhydrous hydrophilic phase comprising at least one hydrophilic vehicle suitable for solubilizing at least one lipophilic, pharmaceutically active agent, and (b) an oily phase comprising at least one oily component which is partially miscible with the at least one hydrophilic vehicle of the anhydrous hydrophilic phase. The desired lipophilic, pharmaceutically active agent or agents to be administered are solubilized in the hydrophilic vehicle or vehicles of the anhydrous hydrophilic phase of these formulations, thus providing a pharmaceutical formulation which not only effectively releases the agent to the host in need of treatment, but which also overcomes many problems associated with previously employed compositions. According to a preferred embodiment, the lipophilic agent is present in the hydrophilic vehicle in a supersaturated or near saturated amount.

In the case of topical application, for example, the anhydrous formulations according to the present invention may be used to provide pharmaceutical compositions which are water washable and yet promote an increased absorption of poorly absorbable lipophilic agents incorporated therein into a host being treated. This result is achieved due to the fact that the lipophilic, pharmaceutically agent administered is present in a solubilized form in the anhydrous hydrophilic phase of these formulations.

The anhydrous hydrophilic phase of the formulations according to the present invention is present in a concentration of from about 1% to about 99%, preferably from about 20% to about 75%, and more preferably from about 25% to about 60%, based upon the total weight of the formulation. The oily phase of the anhydrous formulations according to the present invention is present in a concentration of from about 1% to about 99%, preferably from about 25% to about 80%, and more preferably from about 40% to about 75%, based upon the total weight of the formulation.

As stated, the anhydrous hydrophilic phase of the formulations according to the present invention contains therein at least one hydrophilic vehicle suitable for solubilizing at least one lipophilic, pharmaceutically active agent. Suitable hydrophilic vehicles include, but are not limited to, saturated polyglycolized C8-C10 glycerides, such as the PEG-8 caprylate/caprate glyceride esters sold by Gattefosse Corporation as Labrasol®; PEG-6 caprylic/capric glycerides, such as Softigen 767® sold by Huls Aktiengesellschaft; PEG-60 corn glycerides, such as Crovol M-70® sold by Croda; Ceteareth-20, such as Eumulgin B2® sold by Henkel Corporation; diethyleneglycol monoethylethers, such as Transcutol® sold by Gattefosse Corporation; and other conventional polyethylene glycols referred to as "PEG" materials, such as those discussed in United States Pharmocopeia, Ed. XXII, and in National Formulary, Ed. XVII.

Depending upon the lipophilic, pharmaceutically active agent or agents being administered, the desired consistency of the anhydrous formulation, and the contemplated mode of application, the at least one hydrophilic vehicle employed in the anhydrous formulations according to the present invention may be entirely made up of one or more of the materials described above, or additional carrier vehicles may be present.

The at least one hydrophilic vehicle is preferably present in the anhydrous formulations according to the present invention in a concentration of from about 1% to about 99%, more preferably from about 20% to about 75%, and most preferably from about 25% to about 60%, based upon the total weight of the formulation.

In a preferred embodiment according to the present invention, the at least one hydrophilic vehicle of the anhydrous hydrophilic phase comprises a mixture of a diethyleneglycol monoethyl-ether and a PEG-8 caprylate/caprate glyceride ester. In this situation, the diethyleneglycol monoethyl-ether comprises from about 1% to about 50%, preferably from about 5% to about 40%, and more preferably from about 10% to about 40%, of the formulation; and the PEG-8 caprylate/caprate glyceride ester comprises from about 1% to about 50%, preferably from about 5% to about 40%, and more preferably from about 10% to about 40%, of the formulation.

In another preferred embodiment, the at least one hydrophilic vehicle comprises a mixture of a diethyleneglycol monoethyl-ether and a PEG-6 caprylic/capric glyceride. In this situation, the diethyleneglycol monoethyl-ether comprises from about 1% to about 50%, preferably from about 5% to about 40%, and more preferably from about 10% to about 40%, of the formulation; and the PEG-6 caprylate/capric glyceride comprises from about 1% to about 50%, preferably from about 5% to about 40%, more preferably from about 10% to about 40%, of the formulation.

In yet another embodiment, the at least one hydrophilic vehicle comprises a mixture of a PEG-8 caprylate/caprate glyceride ester and a PEG-6 caprylic/capric glyceride. In this case, the PEG-8 caprylate/caprate glyceride ester comprises from about 1% to about 50%, preferably from about 5% to about 40%, and more preferably from about 10% to about 40%, of the formulation; and said PEG-6 caprylate/capric glyceride comprises from about 1% to about 50%, preferably from about 5% to about 40%, and more preferably from about 10% to about 40%, of the formulation.

The oily phase of an anhydrous formulation according to the present invention, which is partially miscible with the hydrophilic vehicle or vehicles of the anhydrous hydrophilic phase of the formulation, is made up of at least one material commonly referred to in the art as an "oily" component. Physiologically acceptable "oily" components suitable for use in the oily phase of the formulations of the present invention include, but are not limited to, higher aliphatic alcohols such as cetyl alcohol, hexadecyl alcohol, stearyl alcohol, oleyl alcohol and the like; esters of higher aliphatic acids with lower alcohols such as isopropyl myristate, isopropyl palmitate and the like; higher aliphatic acids such as stearic acid, palmitic acid, and the like; hydrocarbons such as liquid paraffin, petrolatum, solid paraffin, microcrystalline wax and the like; esters of higher aliphatic alcohols such as bees wax, spermaceti and the like; natural oils, such as peanut, olive, castor, sesame, rape, and ethereal Oils, and the like; squalene, squalane and the like; and the like; and mixtures thereof.

The "oily" component or components of the oily phase are present preferably in a concentration based upon the total weight of the anhydrous formulation of from about 1% to about 75%, more preferably from about 10% to about 70%, and most preferably from about 20% to about 70%.

According to a preferred embodiment, the oily phase contains at least one "oily" component selected from cetyl alcohol, isopropyl myristate, stearic acid, and mixtures thereof. In the event that all three are present, cetyl alcohol is present preferably in a concentration of from about 0.01% to about 30%, more preferably from about 2% to about 25%; isopropyl myristate is present preferably in a concentration of from about 0.01% to about 40%, more preferably from about 2% to about 30%; and stearic acid is present preferably in a concentration of from about 0.01% to about 20%, more preferably from about 2% to about 15%; all concentrations being based upon the total weight of the anhydrous formulation prepared.

In another preferred embodiment, wherein only cetyl alcohol and stearic acid are present, cetyl alcohol is present in a concentration of from about 0.01% to about 30%, preferably from about 2% to about 25%; and stearic acid is present in a concentration of from about 0.01% to about 40%, preferably from about 2% to about 25%; all concentrations being based upon the total weight of the anhydrous formulation prepared.

In a preferred embodiment, the oily phase of the anhydrous formulations according to the present invention contains one or more emulsifiers. For example, the oily phase may contain one or more partial esters of fatty acids (e.g., lauric, palmitic, stearic, and oleic) or hexitol anhydrides (e.g., hexitans and hexides) derived from sorbitol, such as the commercially available polysorbates sold as Span 60 ®. Other emulsifiers which may be employed are materials derived from adding polyoxyethylene chains to nonesterified hydroxyls of the esters discussed above, such as the commercially available Tween 60 ®. Other emulsifiers which may be used include, but are not limited to, the poly(oxyethylene) poly(oxypropylene) materials marketed by BASF as Pluronic F-68 ®, Pluronic F-127 ® and Pluronic 108 ®. When present, the emulsifier or emulsifiers are present in a concentration of from about 0.01% to about 25%, preferably from about 1% to about 10%, and most preferably from about 2% to about 6%, based upon the total weight of the anhydrous formulation.

The oily phase of the anhydrous formulations according to the present invention also may contain one or more moisturizing enhancers, such as lauryl lactate, caprylic/capric acid triglycerides, lauryl alcohol, diethyl citrate, isopropyl myristate, and the like, and mixtures thereof. Such moisturizing enhancers are present in a concentration of from about 0.01% to about 40%, preferably from about 1% to about 25%, and most preferably from about 5% to about 20%, based upon the total weight of the anhydrous formulation.

In addition to the foregoing, either of the phases may contain a preservative such as benzyl alcohol, or a solution of NaOH in benzyl alcohol, in an amount of from about 0.01% to about 10%, more preferably from about 0.5% to about 5%, and most preferably from about 0.5% to about 3%, based upon the total weight of the anhydrous formulation.

Topical anhydrous formulations according to the present invention are suited for cutaneous application of lipophilic, pharmaceutically active agents which exhibit a primarily local activity in the body near the site of their application, yet which per se exhibit an unsatisfactorily slow and/or poor penetration into and/or permeation through the skin.

Poorly absorbable pharmaceutically active agents which are advantageously incorporated into the anhydrous formulations according to the present invention include, but are not limited to, such diverse agents as poorly absorbable antipsoriatics, cortisones, antimycotics, salicylates, cytostatics, antibiotics, virustatics, antihistamines, UV-absorbers, chemotherapeutics, antiseptics, estrogens, antihydrotics, ethereal oils, scar treatment agents, antifungals, antibacterials, antifolate agents, and cardiovascular agents.

While the anhydrous formulations according to the present invention are useful for administering, in a solubilized form, a wide variety of poorly absorbable lipophilic, pharmaceutically active agents, the inventive formulations are especially useful for administering antipsoriatic agents to hosts suffering from psoriasis. In a preferred embodiment, the lipophilic, pharmaceutically active agents incorporated into the anhydrous formulations according to the present invention are antipsoriatics, such as methotrexate, 5-fluorouracil, and N-($N^4$-(2-Methyl-4-oxo-6-quinazolinyl)methyl)-$N^4$-(prop-2-ynyl)sulfanilyl)indole, hereinafter referred to as "AG85." Particularly preferred is AG85, which has been found to be a very effective antifolate agent and inhibitor of the enzyme thymidylate synthase.

A particularly preferred class of lipophilic agents for use in the present invention are those compounds which inhibit the enzyme thymidylate synthase "TS." Examples of TS inhibiting compounds which may be used in the present invention include, but are not limited to, AG85, 5-fluorouracil, and methotrexate. TS inhibitors which act as antipsoriatics are particularly preferred.

Within the scope of sound medical judgment, the amount of a given lipophilic, pharmaceutically active agent used will vary with the particular condition being treated, the severity of the condition, the duration of the treatment, the nature of the agent employed, the condition of the patient and other factors within the specific knowledge and expertise of the attending physician. The concentration of the lipophilic, pharmaceutically active agent employed is a function not only of the therapeutical requirements described above, but also of the saturation solubility of the active agent in the system. Preferably, the lipophilic agent is present in the at least one hydrophilic vehicle of the anhydrous hydrophilic phase in a supersaturated or near saturated amount.

According to a preferred embodiment, the concentration of the lipophilic agent solubilized in the at least one hydrophilic vehicle of the anhydrous formulation varies from about 0.01% to about 10%, more preferably from about 0.25% to about 5%, and most preferably from about 0.5% to about 2%, based upon the total weight of the formulation. In a preferred embodiment wherein the lipophilic agent is AG85, the compound is solubilized in the formulation in a concentration varying from about 0.01% to about 5%, preferably from about 0.25% to about 4%, and more preferably from about 0.5% to about 3.5%, and most preferably of about 1.25%, based upon the total weight of the formulation.

The anhydrous formulations according to the present invention may comprise additional components, such as pharmaceutically acceptable oils and waxes, and/or such supplementary pharmaceutical adjuvants such as preservatives and antioxidants which are conventionally used in topical formulations, e.g., in conventional bases for ointments, creams, and jellies.

In many cases, it may be advisable to incorporate a structure-forming, thickening or gel-forming agent into the composition. Suitable agents are, in particular, highly dispersed silicic acid, such as the commercially available product Aerosil ®; bentonites; modified montmorillonites, such as alkyl ammonium salts of montmorillonites (e.g., the commercially available Bentone ® products), wherein the alkyl groups may contain 1 to 20 carbon atoms, e.g., dimethyl-dialkylammonium salts wherein the alkyl-groups contain 16 to 18 carbon atoms; and organic structure-forming, thickening and suspending agents, such as cetostearyl alcohol and modified caster oil products (e.g., the commercially available product Antisettle CVP ®).

Other gelling agents which may be used in the anhydrous formulations according to the present invention are those materials capable of increasing the viscosity of the resulting formulation. Suitable gelling agents include, but are not limited to, cellulose derivatives such as carboxymethyl cellulose, cellulose acetate, methyl cellulose, hydroxyethyl cellulose, hydroxypropyl cellulose and the like; natural gums such as gum arabic, xanthum gum, tragacanth gum, guar gum and the like; gelatin; silicon dioxide; synthetic polymers such as carbomers, polyvinylpyrrolidone, polyvinylacetate, polyvinylalcohol, and the like; and mixtures thereof. Gelatin and modified celluloses represent a preferred class of gelling agents. In general, the amount of gelling agent present in the anhydrous formulations according to this invention ranges from about 0% to about 10%, preferably from about 0% to about 5%, of the total weight of the formulation.

In addition to the above described components, the anhydrous formulations of this invention may comprise one or more of the following optional additives: antioxidants such as, for example, ascorbyl palmitate, sodium bisulfite, sodium metabisulfite, BHT, and the like, and mixtures thereof; preservatives such as, for example, potassium sorbate, sodium benzoate, sorbic acid, propyl gallate, benzylalcohol, and the like; sequestering agents such as ethylenediaminetetraacetic acid; flavoring agents such as natural vanillin; coloring agents; buffers such as citric acid and acetic acid; densification agents such as magnesium salts; and mixtures thereof. When present, the total amount of such additional additives typically does not exceed about 5%, more preferably about 2.5% of the total weight of the anhydrous formulation.

Cosmetic and dermatological additives which may be employed in the anhydrous formulations according to the present invention include, but are not limited to, irritation-relieving and anti-inflammatory agents, perfumes and aroma substances, or any other usable additive such as is customary in cosmetics or dermatology for the intended use. In addition, it may sometimes be preferable to adjust the pH of the anhydrous formulation, depending upon its ultimate use, by adding citric acid, lactic acid, sodium hydroxide, tartaric acid and the like.

Of course, all of the materials used in preparing the anhydrous formulations according to the present invention should be toxocilogically safe and compatible with the lipophilic, pharmaceutically active agent to be administered.

In a preferred embodiment according to the present invention, the anhydrous formulation contains cetyl alcohol in an amount of from about 0.01% to about 10%; stearic acid in an amount of from about 0.01% to about 20%; isopropyl myristate in an amount of from about 0.01% to about 20%; and at least one hydrophilic vehicle selected from the group consisting of polyglycolized C8-C10 glycerides, PEG-6 caprylic/capric glycerides, PEG-60 corn glycerides, Ceteareth-20, diethyleneglycol monoethyl-ethers, and mixtures thereof, in an amount of from about 1% to about 75%; based upon the total weight of the formulation.

In another preferred embodiment according to the present invention, the anhydrous formulation contains cetyl alcohol in an amount of from about 0.01% to about 10%; stearic acid in an amount of from about 0.01% to about 30%; and at least one hydrophilic vehicle selected from the group consisting of polyglycolized C8-C10 glycerides, PEG-6 caprylic/capric glycerides, PEG-6 glycerides, Ceteareth-20, diethyleneglycol monoethyl-ethers, and mixtures, in an amount of from about 1% to about 75%; based upon the total weight of the formulation.

In yet another preferred embodiment according to the present invention, the anhydrous formulation contains cetyl alcohol in an amount of from about 0.01% to about 10%; stearic acid in an amount of from about 0.01% to about 20%; isopropyl myristate in an amount of from about 0.01% to about 20%; at least one hydrophilic vehicle selected from the group consisting of polyglycolized C8-C10 glycerides, PEG-6 caprylic/capric glycerides, PEG-60 corn glycerides, Ceteareth-20, diethyleneglycol monoethyl-thers, and mixtures thereof, in an amount of from about 1% to about 75%; and a lipophilic, pharmaceutically active agent in an amount of from about 0.01% to about 5%; based upon the total weight of the formulation. A particularly preferred agent is AG85.

The previous discussion focuses upon the multicomponent anhydrous formulations according to the present invention, which are made up of both an anhydrous hydrophilic phase and an oily phase. It should be noted, however, that in certain cases the anhydrous, hydrophilic vehicles discussed previously may be used to administer lipophilic, pharmaceutically active agents, particularly AG85, to hosts in need of treatment in the absence of an oily phase. Evaluations A-C of Example 9 below illustrate the effectiveness of several preferred hydrophilic vehicles according to the present invention when used in the absence of an oily phase.

Another aspect of the present invention relates to a method of making an anhydrous formulation according to the present invention, which comprises the steps of:

(a) preparing an anhydrous hydrophilic phase comprising at least one hydrophilic vehicle suitable for solubilizing at least one lipophilic, pharmaceutically active agent;

(b) preparing an oily phase which is partially miscible with said at least one hydrophilic vehicle; and (c) combining the two phases to form an anhydrous cream.

The anhydrous formulation may be formed employing widely varying techniques and conditions. For example, homogenization, milling, vortexing, ultrasonication, and microfluidization techniques may be used. The non-limiting examples set forth below illustrate various techniques employed to prepare several anhydrous formulations according to the present invention.

The temperature employed during the formation of the formulations according to the present invention varies depending upon the particular ingredients used. In general, step (a) may be carried out under widely varying conditions, but is typically carried out at a temperature of from about 25° C. to about 100° C., more preferably from about 40° C. to about 100° C., and most preferably from about 50° C. to about 100° C. Step (b) may be carried out under widely varying conditions, but is typically carried out at a temperature of from about 25° C. to about 75° C., more preferably from about 40° C. to about 80° C., and most preferably from about 50° C. to about 75° C. Step (c) may be carried out under widely varying conditions, but is typically carried out at a temperature of from about 25° C. to about 100° C., more preferably from about 40° C. to about 80° C., and most preferably from about 50° C. to about 75° C.

A further aspect of the present relates to a method of administering a lipophilic, pharmaceutically active agent to a host in need of treatment, comprising solubilizing a pharmaceutically effective amount of the agent in the anhydrous hydrophilic phase of an anhydrous formulation according to the present invention and then administering said formulation to the host being treated. Preferably, the agent is present in the hydrophilic vehicle in a supersaturated or near saturated amount.

Another aspect of the present invention relates to a method of treating skin dermatoses, such as psoriasis, comprising administering to a host in need of such treatment a pharmaceutically effective amount of a lipophilic, pharmaceutically active agent by solubilizing the agent in the anhydrous hydrophilic phase of an anhydrous formulation according to the present invention. Preferably, the agent is present in the hydrophilic vehicle in a supersaturated or near saturated amount.

A yet further aspect of the present invention relates to a method of enhancing the absorption of a lipophilic, pharmaceutically active agent into a host being treated, comprising solubilizing the agent in the anhydrous hydrophilic phase of an anhydrous formulation according to the present invention. Preferably, the agent is present in the hydrophilic vehicle in a supersaturated or near saturated amount.

EXAMPLES

The following examples provide detailed illustrations of the formulations according to the present invention. These examples are not intended, however, to limit or restrict the scope of the invention in any way, and should not be construed as providing methods, formulations, or ingredients which must be utilized exclusively to practice the present invention. Unless otherwise indicated, all concentrations provided relate to the weight percent of the particular component based upon the total weight of the anhydrous formulation under evaluation.

EXAMPLE 1

Anhydrous formulations according to the present invention useful for administering lipophilic compounds such as AG85 were prepared as follows.

| Formulation I | |
|---|---|
| Oily Phase | Anhydrous Hydrophilic Phase |
| 5.6% Stearic Acid | 84.3% Softigen 760 |
| 4.5% Cetyl Alcohol | 1.2% Benzyl Alcohol |
| 2.2% Span 60 | 2.2% NaOH |

Formulation I was prepared as follows. The oily phase ingredients were combined in a 30 ml beaker, and then stirred while heating to approximately 60°-65° C. The Softigen 767 anhydrous hydrophilic phase ingredient was heated in a 150 ml beaker to approximately 65°-70° C. Using a pasteur pipet, the oily phase was added dropwise to the anhydrous hydrophilic phase with rapid mixing. Before congeling set in, the benzyl alcohol and NaOH ingredient were added to the mixture. After all of the ingredients had been added, the resulting mixture was mixed for approximately 2 additional minutes. The mixture was then subjected to homogenization at a 50% rate using a small wing generator. After 5 minutes, homogenization was increased to a 100% rate, and then, after about 15 minutes, homogenization was stopped. Throughout the homogenization and up to 5 minutes after it was completed, the mixture was subjected to magnetic stirring. The product was transferred to 3×30 ml amber glass bottles and allowed to cool completely overnight. The resulting product was very soft and fluid-like.

| Formulation II | |
|---|---|
| Oily Phase | Anhydrous Hydrophilic Phase |
| 8.0% Isopropyl Myristate | 78.3% Labrasol |
| 2.3% Span 60 | 1.0% Benzyl Alcohol |
| 4.7% Cetyl Alcohol | |
| 5.7% Stearic Acid | |

Formulation II was prepared as follows. The oily phase ingredients were combined in a 30 ml beaker, and then stirred while heating to approximately 63° C. After heating the Labrasol anhydrous hydrophilic phase ingredient to approximately 70° C., the oily phase was added dropwise to the anhydrous hydrophilic phase under rapid mixing. Before congeling set in, the benzyl alcohol ingredient was added to the mixture. After all of the ingredients had been added, the resulting mixture was mixed for an additional minute. The mixture was then subjected to homogenization for 5 minutes at a 50% rate using a small generator, during which the product became thicker after approximately 4 minutes. After about 2 minutes of homogenization, ice was used on the outside of the beaker for cooling purposes to obtain a final product temperature after homogenization of about 31° C. The product was then transferred to 3×30 ml amber glass bottles and allowed to cool completely overnight.

| Formulation III | |
|---|---|
| Oily Phase | Anhydrous Hydrophilic Phase |
| 8.0% Isopropyl Myristate | 78.3% Softigen 767 |
| 2.3% Span 60 | 1.0% Benzyl Alcohol |
| 4.7% Cetyl Alcohol | |
| 5.7% Stearic Acid | |

Formulation III was prepared as follows. The oily phase ingredients were heated to approximately 58° C. while undergoing gentle stirring. The Softigen 767 anhydrous hydrophilic phase ingredient was heated to approximately 60° C. The oily phase was added dropwise to the anhydrous hydrophilic phase, and the resulting mixture was mixed for about 1 minute. The benzyl alcohol ingredient was added to the mixture before congeling set in. The mixture was then subjected to homogenization for 5 minutes at a 50% rate. Using ice on the outside of the beaker, the product after homogenization was brought to a temperature of about 35° C. The product was then stirred for another 2 minutes to cool the product to about 30° C., at which point the product was transferred to 3×30 ml amber glass bottles and allowed to cool completely.

EXAMPLE 2

Anhydrous formulations according to the present invention containing AG85 were prepared as follows.

| Formulation IV | |
|---|---|
| Oily Phase | Anhydrous Hydrophilic Phase |
| 7.5% Cetyl Alcohol | 0.5% AG85 |
| 7.5% Stearic Acid | 72.5% Labrasol |
| 10% Isopropyl Myristate | 2.0% NaOH/Benzyl Alcohol (500 mg/20 ml) |

Formulation IV was prepared as follows. The oily phase ingredients were mixed in a 30 ml beaker and heated to approximately 58° C. while undergoing stirring, and the Labrasol component was heated in a 150 ml beaker to approximately 58° C. while undergoing stirring. The AG85 component was then solubilized in the Labrasol slowly over a 15 minute period while undergoing rapid stirring. The oily phase components were then added dropwise to the Labrasol/AG85 mixture over 5 minutes while stirring. Before congeling set in, the NaOH/Benzyl Alcohol mixture was added to the mixture. The mixture was then subjected to homogenization for 5 minutes at a 50% rate using a small wing generator, during which the mixture was cooled to obtain a final product temperature of about 33° C. The product then was transferred to 4×102 aluminum tubes.

| Formulation V | |
|---|---|
| Oily Phase | Anhydrous Hydrophilic Phase |
| 10% Isopropyl Myristate | 0.5% AG85 |
| 7.5% Cetyl Alcohol | 72.5% Softigen 767 |
| 7.5% Stearic Acid | 2.0% NaOH/Benzyl Alcohol (500 mg/20 ml) |

Formulation V was prepared as follows. The Softigen 767 was heated in a 150 ml beaker to approximately 59.6° C. while undergoing moderate stirring, and then the AG85 component was then solubilized in the Softigen 767 slowly over a 21 minute period while undergoing rapid stirring. The resulting mixture was stirred an additional 3 minutes to ensure complete dissolution. The oily phase ingredients were then mixed in a 30 ml beaker and heated to approximately 59° C. while undergoing moderate stirring, and the resulting mixture was added dropwise to the Softigen 767/AG85 mixture over 5 minutes while stirring. The NaOH/Benzyl Alcohol component was added to this mixture before congeling set in. The mixture was then subjected to homogenization for 5 minutes at a 50% rate using a small wing generator. The mixture was cooled during homogenization to obtain a final product temperature of about 37° C. The product was then stirred for an additional 4 minutes to cool the product to 34° C., and the product was transferred to 1×102 aluminum tubes.

| Formulation VI | |
|---|---|
| Oily Phase | Anhydrous Hydrophilic Phase |
| 10% Isopropyl Myristate | 0.5% AG85 |
| 7.5% Cetyl Alcohol | 72.5% Croval M70 |
| 7.5% Stearic Acid | 2.0% NaOH/Benzyl Alcohol (500 mg/20 ml) |

Formulation VI was prepared as follows. The AG85 and Croval M70 components were heated in a 150 ml beaker to approximately 59° C. while undergoing slow stirring, and the oily phase ingredients were mixed in a 30 ml beaker and heated to approximately 62° C. while undergoing slow stirring. The oily phase mixture was then added dropwise to the AG85/Croval M70 mixture under maximum stirring, and the resulting composition was stirred for an additional minute. Before congeling set in, the NaOH/Benzyl Alcohol component was added to the mixture. The resulting mixture was cooled and then subjected to homogenization for 5 minutes at a 50% rate. The mixture was stirred at a maximum rate both during homogenization and for an additional minute after homogenization was stopped. The resulting mixture was then transferred to clear glass vials and an aluminum tube, at which point it was subjected to sonication for 1 minute at 30° C. to remove air bubbles.

| Formulation VII | |
|---|---|
| Oily Phase | Anhydrous Hydrophilic Phase |
| 10% Isopropyl Myristate | 0.5% AG85 |
| 7.5% Cetyl Alcohol | 72.5% Eumulgin B2 |
| 7.5% Stearic Acid | 2.0% NaOH/Benzyl Alcohol (500 mg/20 ml) |

Formulation VII was prepared as follows. The Eumulgin B2 was heated in a 250 ml beaker to approximately 58° C. while undergoing maximum stirring, and the AG85 component was slowly solubilized in the Eumulgin B2. The oily phase ingredients were mixed in a 30 ml beaker and heated to approximately 59° C. while undergoing slow stirring, and the resulting oily phase mixture was then added dropwise to the AG85/Eumulgin. During the addition and for 2 minutes thereafter, the mixture was subjected to maximum stirring, and the NaOH/Benzyl Alcohol component was added before congeling set in. The outside of the beaker was subjected to cooling, and the mixture was subjected to homogenization for 5 minutes at a 50% rate. The temperature of the mixture after cooling and homogenization was 38° C. The resulting product was stirred for an additional minute at maximum speed and then transferred to 4 clear vials and one aluminum tube.

| Formulation VIII | |
|---|---|
| Oily Phase | Anhydrous Hydrophilic Phase |
| 15% Cetyl Alcohol | 0.5% AG85 |
| 15% Stearic Acid | 47.5% Transcutol |
| 20% Isopropyl Myristate | 2.0% NaOH/Benzyl Alcohol (500 mg/20 ml) |

Formulation VIII was prepared as follows. The Transcutol was heated in a 150 ml beaker to approximately 59° C. while undergoing moderate stirring. The AG85 component was then added slowly to the Transcutol until solubilization was complete. The oily phase ingredients were mixed in a 100 ml beaker, heated to approximately 65° C. while undergoing slow stirring and then added dropwise to the AG85/Transcutol mixture while stirring. The mixture was then stirred for an additional minute. The beaker was cooled with ice, and the mixture was subjected to homogenization for 5 minutes at a 50% rate using a small generator while undergoing stirring. The (NaOH/Benzyl Alcohol) component was then added to the mixture before congeling set in. The mixture after homogenization had a temperature of about 26° C. The mixture was mixed for an additional minute after homogenization was complete, and the resulting product was transferred to 5 clear vials and an aluminum tube.

| Formulation IX | |
|---|---|
| Oily Phase | Anhydrous Hydrophilic Phase |
| 15% Cetyl Alcohol | 56.5% Labrasol |
| 15% Stearic Acid | 0.5% AG85 |
| 10% Isopropyl Myristate | 1.0% NaOH |
| | 2.0% Benzyl Alcohol |

Formulation IX was prepared as follows. The oily phase ingredients were mixed in a 100 ml beaker and heated to approximately 60° C. while undergoing stirring. The Labrasol was heated in a 150 ml beaker to approximately 60° C. while undergoing rapid stirring, and the AG85 was slowly added to this mixture until dissolution was complete. The oily phase was then added dropwise to the Labrasol/AG85 mixture, and the resulting mixture was subjected to homogenization for 2 minutes at a 50% rate. Prior to congeling setting in, the NaOH and benzyl alcohol components were added to the mixture.

Formulation X

A formulation made up of 1% w/w of AG85, 20% w/w of an oily phase component, and 79% w/w of an anhydrous hydrophilic phase component was prepared as follows. First, an anhydrous hydrophilic phase solution having 45% Labrasol, 45% Transcutol, and 10% lauryl lactate was prepared, and the AG85 component was solubilized therein. An oily phase having 35.7% cetyl alcohol, 35.7% stearic acid, 9.1% Span 80, and 10.0% Tween 60 was prepared and added dropwise to the anhydrous hydrophilic phase/AG85 mixture. Before congeling set in, 9.5% of a solution of 500 mg NaOH in 20 ml of benzyl alcohol was added to the mixture.

Formulation XI

A formulation made up of 1% w/w of AG85, 20% w/w of an oily phase component, 69% w/w of an anhydrous hydrophilic phase component, and 10% w/w of Myritol 318 ® (caprylic/capric triglycerides manufactured by Henkel Corp.) was prepared as follows. First, an anhydrous hydrophilic phase solution having 50% Labrasol and 50% Transcutol was prepared, and then the AG85 component solubilized therein. An oily phase component having 35.7% cetyl alcohol, 35.7% stearic acid, 9.1% Span 80, and 10.0% Tween 60 was prepared and added dropwise to the anhydrous hydrophilic phase/AG85 mixture. Prior to congeling setting in, 9.5% of a solution of 500 mg NaOH in 20 ml of benzyl alcohol was added to the mixture.

Formulation XII

Formulation XII was prepared as follows. First, an oily phase component made up of 35.7% cetyl alcohol, 35.7% stearic acid, 9.1% Span 80, and 10% Tween 60 was prepared. Two anhydrous hydrophilic phase vehicles were then prepared. The first vehicle ("vehicle-1") was a solution made up of 48.976% Transcutol, 48.976% Labrasol, 0.0499% BHT, and 1.999% AG85. The second vehicle ("vehicle-2") was a solution of 49.975% Transcutol, 49.975% Labrasol, and 0.05% BHT. The oily phase ingredients were heated to about 60° C. while undergoing slow stirring. The anhydrous hydrophilic phase was then prepared by mixing vehicle-1, vehicle-2 and a lauryl lactate component, and then heating this mixture to about 60° C. while undergoing moderate stirring. The oily phase was then slowly added dropwise to the anhydrous hydrophilic phase over a one minute interval while gradually increasing the mixing rate. Prior to congeling setting in, 9.5% of a solution of 500 mg of NaOH in 20 ml of benzyl alcohol was added to the mixture. The mixture was then cooled to room temperature in an ice bath while continuing the mixing at maximum speed. The resulting product, which was made up of 20% oily phase, 20% lauryl lactate, 50% vehicle-1, and 10% vehicle-2, was then transferred to clear glass vials.

EXAMPLE 3

In addition to the foregoing, the following additional formulations were prepared employing similar processes to those set forth above. In each case, the oily phase was made up of 35.7% cetyl alcohol, 35.7% stearic acid, 9.1% Span 80, and 10% Tween 60, and the "AG85 Solution" was made up of 48.975% Transcutol, 48.975% Labrasol, 0.05% BHT, 2% AG85, and 9.5% of a solution of 500 mg of NaOH in 20 ml of benzyl alcohol. The final concentration of AG85 in each of the formulations was 1%.

| Formulation XIII |
| --- |
| 50% AG85 Solution |
| 10% Diethyl Citrate |
| 20% Lauroglycol |
| 20% Oily Phase |

| Formulation XIV |
| --- |
| 50% AG85 Solution |
| 10% Diethyl Citrate |
| 20% Caprylic/Caprate Triglycerides |
| 20% Oily Phase |

| Formulation XV |
| --- |
| 50% AG85 Solution |
| 10% Diethyl Citrate |
| 20% Lauryl Lactate |
| 20% Oily Phase |

| Formulation XVI |
| --- |
| 50% AG85 Solution |
| 5% Labrasol |
| 5% Transcutol |
| 20% Lauryl Lactate |
| 20% Oily Phase |

| Formulation XVII |
| --- |
| 50% AG85 Solution |
| 10% Diethyl Citrate |
| 20% Lauroglycol |
| 20% Oily Phase |

EXAMPLE 4

Additional anhydrous formulations according to the present invention were prepared as follows. In each case, the "AG85 Solution" was made up of 48.975% Transcutol, 48.975% Labrasol, 0.05% BHT, and 2% AG85. To prepare the formulations, all of the ingredients except the AG85 Solution were combined and heated to a temperature of about 65° C. After a uniform melt was achieved, the mixture was cooled to about 50°-55° C. The AG85 Solution was then added, and the mixture was subjected to mixing until thickening occurred. Sedafos 75 ® is a palmito-stearate glycol manufactured by Gattefosse, S.A. Compitrol 888 ® is a glyceryl behenate NF manufactured by Gattefosse, S.A. Labrafil M2130CS materials are saturated polyglycolized glycerides and polyethylene glycol ethers manufactured by Gattefosse S.A.

| Formulation XVIII |
| --- |
| 50% AG85 Solution |
| 25% Sedafos 75 |
| 5% Compitrol 888 |
| 10% Labrafil M2130CS |
| 10% Caprylic/Capric Triglycerides |

| Formulation XIX |
| --- |
| 50% AG85 Solution |
| 25% Sedafos 75 |
| 5% Compitrol 888 |
| 10% Labrafil M2130CS |
| 10% Lauryl Lactate |

| Formulation XX |
| --- |
| 50% AG85 Solution |
| 20% Sedafos 75 |
| 5% Compitrol 888 |
| 10% Labrafil M2130CS |
| 10% Caprylic/Capric Triglycerides |

EXAMPLE 5

The following formulations according to the present invention also were prepared. In each case, the "AG85 Solution" was made up of 48.975% Transcutol, 48.975% Labrasol, 0.05% BHT, and 2% AG85. To prepare the formulations, all of the ingredients except the AG85 Solution and the benzyl alcohol were combined and heated to a temperature of about 70° C. After a uniform melt was achieved, the mixture was cooled, and the AG85 Solution was added. Prior to congeling setting in, the benzyl alcohol was added. The mixture was subjected to mixing until thickening occurred. All of the products demonstrated good results. Arlacel 165 ® is a glyceryl monostearate/polyoxyethylene stearate manufactured by ICI Americas. Wecobee M is an hydrogenated vegetable oil.

| Formulation XXI |
| --- |
| 50% AG85 Solution |
| 2% Benzyl Alcohol |
| 24% Sedafos 25 |
| 4.8% Compitrol 888 |
| 9.6% Labrafil M2130CS |
| 9.6% Lauryl Lactate |

| Formulation XXII |
| --- |
| 50% AG85 Solution |
| 2% Benzyl Alcohol |
| 10% Arlacel 165 |
| 3% Compitrol 888 |
| 25% Labrafil M2130CS |
| 10% Lauryl Lactate |

| Formulation XXIII |
| --- |
| 50% AG85 Solution |
| 2% Benzyl Alcohol |
| 10% Arlacel 165 |
| 3% Compitrol 888 |
| 5% Labrafil M2130CS |
| 10% Lauryl Lactate |
| 20% Wecobee M |

| Formulation XXIV |
| --- |
| 25% AG85 Solution |
| 2% Benzyl Alcohol |
| 10% Arlacel 165 |
| 3% Compitrol 888 |
| 30% Labrafil M2130CS |
| 10% Lauryl Lactate |
| 20% Wecobee M |

EXAMPLE 6

Additional anhydrous formulations were prepared as follows. In each case, the "AG85-1 Solution" was made up of 48.975% Transcutol, 48.975% Labrasol, 0.1% BHT, and 2% AG85, and the "AG85-2 Solution" was made up of 48.4% Transcutol, 48.4% Labrasol, 0.1% BHT and 3% AG85. To prepare the formulations, all of the ingredients except the respective AG85 Solution and the benzyl alcohol were combined and heated to a temperature of about 70° C. After a uniform melt was achieved, the mixture was cooled, and the AG85 Solution was then added. The mixture was then subjected to mixing until thickening occurred. Before congeling set in, the benzyl alcohol was added with mixing.

| Formulation XXV |                |
|-----------------|----------------|
| 50%             | AG85-1 Solution|
| 2%              | Benzyl Alcohol |
| 10%             | Arlacel 165    |
| 3%              | Compitrol 888  |
| 25%             | Labrafil M2130CS |
| 10%             | Lauryl Lactate |

| Formulation XXVI |                |
|------------------|----------------|
| 50%              | AG85-2 Solution|
| 2%               | Benzyl Alcohol |
| 10%              | Arlacel 165    |
| 3%               | Compitrol 888  |
| 25%              | Labrafil M2130CS |
| 10%              | Lauryl Lactate |

| Formulation XXVII |                |
|-------------------|----------------|
| 50%               | AG85-1 Solution|
| 2%                | Benzyl Alcohol |
| 10%               | Arlacel 165    |
| 3%                | Compitrol 888  |
| 25%               | Labrafil M2130CS |
| 5%                | Lauryl Lactate |
| 5%                | Caprylic/Capric Triglycerides |

EXAMPLES 7

The following additional anhydrous formulations according to the present invention were also prepared. In each of the formulations described, the lipophilic agent is present in the hydrophilic vehicle of the anhydrous hydrophilic phase at near saturation.

| Formulation XXVIII | |
|---|---|
| Oily Phase | Anhydrous Hydrophilic Phase |
| 10% Arlacel 165 | 1.25% AG85 |
| 3% Compritol 888 | 24.35% Transcutol |
| 25% Labrafil M2130CS | 24.35% Labrasol |
| 10% Lauryl Lactate | 0.05% BHT |
|  | 2% Benzyl Alcohol |

Formulation XXVIII was prepared as follows. The AG85 component was solubilized in a mixture of the Transcutol, Labrasol and BHT components, and the oily phase materials were heated separately to a temperature of 70°. After melting, the oily phase materials were added to the Transcutol/Labrasol/BHT/AG85 mixture under mixing. Prior to congeling setting in, the benzyl alcohol was added to the mixture.

| Formulation XXIX | |
|---|---|
| Oily Phase | Anhydrous Hydrophilic Phase |
| 7% Cetyl Alcohol | 0.75% AG85 |
| 7% Stearic Acid | 20% Ceraphyl 31 |
| 1.9% Span 80 | 59.2% Labrasol |
| 2.1% Tween 60 | 0.05% BHT |
|  | 2% Benzyl Alcohol |

Formulation XXIX was prepared as follows. The AG85 was added slowly to a mixture of the Labrasol and BHT components, the mixture having been heated to 85° prior to the addition of the AG85. After all of the AG85 had been added, the Ceraphyl 31 was added to the mixture. The oily phase ingredients were then heated to 85° in a 150 ml beaker, and then slowly added to the Labrasol/ BHT/AG85/Ceraphyl mixture as a slow steady stream. After all of the oily phase had been added, the temperature of the resulting mixture was maintained at 70° for 2 minutes. The mixture was then subjected to homogenization at a 50% rate for 6 minutes. Prior to congeling setting in, the benzyl alcohol was added to the mixture.

| Formulation XXX | |
|---|---|
| Oily Phase | Anhydrous Hydrophilic Phase |
| 12% Cetyl Alcohol | 0.75% AG85 |
| 12% Stearic Acid | 10% Ceraphyl 31 |
| 1.9% Span 80 | 59.2% Labrasol |
| 2.1% Tween 60 | 0.05% BHT |
|  | 2% Benzyl Alcohol |

Formulation XXX was prepared as follows. The AG85 was added slowly to a mixture of the Labrasol and BHT components, the mixture having been heated to 79° prior to the addition of the AG85. After all of the AG85 had been added, the Ceraphyl 31 was added to the mixture. The oily phase ingredients were heated to 83° in a 50 ml beaker, and then slowly added to the Labrasol/BHT/ AG85/Ceraphyl mixture as a slow steady stream wile undergoing magnetic stirring at a maximum rate. After all of the oily phase had been added, the temperature of the resulting mixture was maintained at 45° for 2 minutes. The mixture was then subjected to propeller mixing at approximately 700 rpm. When the mixture attained a temperature of 40° C., the benzyl alcohol was added to the mixture, and mixing continued until a temperature of approximately 35° C. was achieved.

| Formulation XXXI | |
|---|---|
| Oily Phase | Anhydrous Hydrophilic Phase |
| 10% Arlacel 165 | 1% AG85 |
| 3% Compitrol 888 | 24.475% Transcutol |
| 25% Labrafil M2130CS | 24.475% Labrasol |
| 10% Ceraphyl 31 | 0.05% BHT |
|  | 2% Benzyl Alcohol |

Formulation XXXI was prepared as follows. The oil phase components were combined in a 400 ml beaker and heated to 70° C. while undergoing slow magnetic stirring. The AG85 was added slowly to a mixture of the Labrasol, Transcutol and BHT components, the mixture having been heated to 90° prior to the addition of the AG85. After all of the AG85 had been added and a clear solution obtained, the oily phase materials were added to the AG85 solution in a slow steady stream while undergoing maximum stirring. After all of the oily phase had been added, the temperature of the resulting mixture was maintained at 48° for 2 minutes, and mixing was continued. The mixture was then subjected to homogenization at a 50% rate, following which the product was cooled using an ice bath. Prior to congeling setting in, the benzyl alcohol was added to the mixture. The product was then subjected to additional mixing at increasing speeds until a temperature of less than 30° C. was obtained.

| Formulation XXXII |                  |
|-------------------|------------------|
| 54%               | Labrafil M2130CS |
| 6%                | Arlacel 165      |
| 3%                | Compitrol 888    |
| 10%               | Lauryl Lactate   |

-continued

| Formulation XXXII |
|---|
| 25% AG85 Solution |
| 2% Benzyl Alcohol |

Formulation XXXII was prepared as follows. First, the AG85 Solution was prepared by combining two different solutions. The first was made up of 49.975% Transcutol, 49.975% Labrasol and 0.05% BHT. The other was made up of 49% Transcutol, 49% Labrasol, 0.05% BHT and 2% AG85. The AG85 Solution was then heated to 60°–70° C. An oily phase component was prepared by mixing the Labrafil M2130CS, Arlacel, Compritol and lauryl lactate, and then heating the mixture to 70° C. The oily phase was then added to the AG85 Solution under mixing until a uniform was obtained. The benzyl alcohol was added at approximately 25° C., prior to congeling setting in. The resulting cream was smooth, uniform and had a good viscosity.

EXAMPLE 8

The following formulations according to the present invention also were prepared. "AG85 Solution-1," which was a 2% AG85 solution in Labrasol. "AG85 Solution-2," which was a 1.5% AG85 solution, was prepared by mixing 0.125 g AG85 with 24.87 g of a mixture of 1 g of AG85 and 99 g of Softigen. "AG85 Solution-3," which was a 2.5% AG85 solution, was prepared by mixing 1.25 g AG85, 0.025 g BHT, 24.36 g Transcutol, and 24.36 g Labrasol. To prepare the formulations, all of the ingredients except the respective AG85 Solution and the benzyl alcohol were combined and heated to a temperature of about 70° C. After a uniform melt was achieved, the mixture was cooled, and the appropriate AG85 Solution was added. Prior to congeling setting in, the benzyl alcohol was added. The mixture was subjected to mixing until thickening occurred. The resulting cream formulations XXXIII–XXXVI contained AG85 in amounts of 1%, 0.75%, 1.25% and 0.625% respectively. In each of the formulations described, the lipophilic agent is present in the hydrophilic vehicle of the anhydrous hydrophilic phase at near saturation.

| Formulation XXXIII |
|---|
| 50% AG85 Solution-1 |
| 2% Benzyl Alcohol |
| 23% Labrafil M2130CS |
| 10% Lauryl Lactate |
| 15% Cetyl Alcohol |

| Formulation XXXIV |
|---|
| 50% AG85 Solution-2 |
| 2% Benzyl Alcohol |
| 23% Labrafil M2130CS |
| 10% Lauryl Lactate |
| 15% Cetyl Alcohol |

| Formulation XXXV |
|---|
| 50% AG85 Solution-3 |
| 2% Benzyl Alcohol |
| 21% Labrafil M2130CS |
| 10% Lauryl Lactate |
| 17% Cetyl Alcohol |

| Formulation XXXVI |
|---|
| 25% AG85 Solution-3 |
| 2% Benzyl Alcohol |
| 54% Labrafil M2130CS |
| 10% Lauryl Lactate |
| 6% Arlacel 165 |

-continued

| |
|---|
| 3% Compitrol 888 |

SKIN PERMEATION EVALUATIONS

The following tests were carried out to evaluate the in vitro skin permeation of AG85 both from various preferred formulations according to the present invention and from various preferred vehicles for use in the present invention. Several of the evaluations are directed to formulations set forth in the previous examples. The tests were conducted as follows.

A $PEG400:H_2O$ (3:2) solution was used as receptor phase in a Franz cell and allowed to equilibrate at 37° C. for about 30 minutes. A skin sample was cut in segments large enough to cover the cell and then soaked in distilled $H_2O$ for about 5 minutes. After measuring the thickness of the sample, the sample was placed on top of the cell, and a rubber gasket/O-ring apparatus having a glass top was used to fix the sample in place. The vehicle or formulation being tested was then administered to the sample, and the weight of the vehicle/formulation used was calculated.

At the end of the experiment, the receptor solution was filtered through a 0.45 $\mu$ nylon membrane, and the vehicle/formulation remaining on the surface of the skin was removed. The surface of the skin was then rinsed with a $PEG400/H_2O$ (3:2) solution. After removing any excess $PEG400/H_2O$ solution, the skin sample was removed from the cell and pat dry.

The sample was then taped, cut in small pieces, and placed in vials containing 1.0 ml MeOH. The vials were then sonicated for approximately 3 hours. After sonication, the solutions formed in the vials were filtered through a 0.45 $\mu$ nylon filter and submitted for assay. The examples illustrate that both the amount of AG85 released and the amount in the skin is significantly higher for anhydrous formulations according to the present invention, compared to the control formulations prepared with propylene glycol ethanol. The products also demonstrate increased penetration after rubbing.

EXAMPLE 9

The following tests were carried out to examine the effectiveness of using various vehicles for solubilizing topically administering lipophilic compounds such as AG85.

Evaluation A

Study 0692

The receptor vehicle for this evaluation was an aqueous 50% PEG400 solution. The average thicknesses of the skin samples used in this evaluation were 0.60±0.13, 0.65±0.05 and 0.68±0.13 mm, respectively. The skin samples were taken from a black male.

| Formulation | Amount Released | Recovery from Skin | Recovery from Tape | Recovery from Residue |
|---|---|---|---|---|
| 0.5% AG85 in Labrasol | 0.17 $\mu$g | 2.00 ± 0.57 $\mu$g | 2.36 ± 1.00 $\mu$g | 399 ± 115 $\mu$g |
| 0.5% AG85 in Transcutol | 0.14 $\mu$g | 1.44 ± 0.44 $\mu$g | 0.87 ± 0.03 $\mu$g | 337 ± 11 $\mu$g |
| 0.5% AG85 in Softigen | — | 1.46 ± 0.34 $\mu$g | 2.09 ± 1.00 $\mu$g | 313 ± 23 $\mu$g |

Evaluation B

Study 0792

The receptor vehicle for this evaluation was an aqueous 40% PEG400 solution, and the run time for the evaluation was 48 hours. The average thicknesses of the skin samples used in this evaluation were 0.24±0.03, 0.28±0.02 and 0.57±0.08 mm, respectively. The skin samples were taken from a black male.

| Formulation | Amount Released | Recovery from Skin | Recovery from Tape | Recovery from Residue |
|---|---|---|---|---|
| 0.5% AG in Crovol M-70 | 0.68 μg | 1.32 ± 0.61 μg | 1.50 ± 1.06 μg | 449 ± 14 μg |
| 0.5% AG85 in Labrasol | 1.05 μg | 1.22 ± 0.63 μg | 1.78 ± 1.00 μg | 550 ± 39 μg |
| 0.5% AG85 in Labrasol | 0.56 μg | 1.77 ± 0.33 μg | 1.15 ± 0.06 μg | 589 ± 27 μg |

Evaluation C

Study 1992

The receptor vehicle for this evaluation was an aqueous 60% PEG400 solution, and sampling was conducted after 18 hours. The skin donor was a white male.

| | Amount Applied | Amount Released | Amount in skin | Skin Thickness | Cell No. | μg/mg skin |
|---|---|---|---|---|---|---|
| AG85 in 100% Transcutol | Saturated | 0.0 μg | 1.43 | 0.50 mm | 1 | 2.86 |
| | | 0.0 μg | 2.50 μg | 0.55 mm | 2 | 4.55 |
| | | 0.0 μg | 1.14 μg | 0.58 mm | 3 | 1.97 |
| AG85 in 100% Labrasol | Saturated | 0.36 μg | 1.35 μg | 0.59 mm | 4 | 2.29 |
| | | 0.0 μg | 1.63 μg | 0.82 mm | 5 | 1.99 |
| | | 0.0 μg | 1.25 μg | 0.64 mm | 6 | 1.95 |
| AG85 in 100% Softigen | Saturated | 0.0 μg | 1.14 μg | 0.58 mm | 7 | 1.97 |
| | | 0.0 μg | 1.04 μg | 0.68 mm | 8 | 1.53 |
| | | 1.52 μg | 1.08 μg | 0.68 mm | 9 | 1.59 |
| AG85 in 1:1 Trans:Lab | Saturated | 0.31 μg | 1.32 μg | 0.64 mm | 11 | 2.06 |
| | | 0.0 μg | 1.33 μg | 0.73 mm | 12 | 1.82 |
| | | 0.47 μg | 4.20 μg | 0.47 mm | 13 | 8.94 |
| AG85 in 1:1 Trans:Soft | Saturated | ND | ND | 0.72 mm | 14 | ND |
| | | 3.67 μg | 1.17 μg | 0.42 mm | 15 | 1.63 |
| | | 0.39 μg | 1.09 μg | 0.56 mm | 16 | 1.95 |
| AG85 in 1:1 Lab:Soft | Saturated | 0.0 μg | 0.71 μg | 0.50 mm | 17 | 1.42 |
| | | 0.0 μg | 1.21 μg | 0.52 mm | 18 | 2.33 |
| | | 0.0 μg | 1.32 μg | 0.52 mm | 19 | 2.59 |

*ND => None detected

EXAMPLE 10

The following tests were carried out to examine the effectiveness of several multicomponent formulations according to the present invention for use in topically administering lipophilic compounds such as AG85. In each of the evaluations, the "Control" formulation was a propylene glycol/ethanol (1:4) solution containing 0.1% AG85.

Evaluation D

Study 292

The receptor vehicle for this evaluation was an aqueous 40% PEG400 solution. The recovery of AG85 from skins, tapes and the formulation residue was determined after 48 hours. The amount of AG85 delivered into the receptor vehicle was determined after 24 hours. The average thickness of the skin used in this evaluation was 0.22+0.07 mm. The skin samples were taken from a black male. The results illustrated increased flux for Formulation IV, as compared to the control.

| Formulation | Amount Released | Recovery from Skin | Recovery from Tape | Recovery from Residue |
|---|---|---|---|---|
| Control | 14.21 μg or 0.66 μg/cm²hr | 6.11 ± 0.95 μg | 2.93 ± 1.89 μg | 25.28 ± 9.38 μg |
| IV | 78.53 μg or 3.64 μg/cm²hr | 2.08 ± 1.09 μg | 1.34 ± 0.98 μg | 412 ± 139 μg |
| V | 4.84 μg or 0.22 μg/cm²hr | 1.21 ± 0.73 μg | 2.98 ± 2.11 μg | 475 ± 51 μg |

| | Average AG-85 Delivered Across 0.9 cm2 of Human Cadaverous Skin Over 24 Hours | | | |
|---|---|---|---|---|
| | Whole Skin | | Stripped Skin | |
| Formulation | AMOUNT (μg) | FLUX (μg/cm²h) | AMOUNT (μg) | FLUX (μg/cm²h) |
| Control | 14.2 | 0.66 | 0.73 | 0.03 |
| IV | 78.5 | 3.63 | 49.13 | 2.27 |
| V | 4.8 | 0.22 | 8.02 | 0.37 |

Evaluation E

Study 1792

The receptor vehicle for this evaluation was an aqueous 60% PEG400 solution, and sampling was conducted at 24 and 72 hours. The skin donor was a white male.

| Formulation | Amount of AG85 applied | Amount Released (μg) 24 hr | Amount Released (μg) 72 hr | Amount in skin μg | Skin Thickness |
|---|---|---|---|---|---|
| XIII | 1.79 mg | 18.92 | 4.71 | 5.61 | 0.50 mm |
|  | 1.92 mg | 34.65 | 3.60 | 4.52 | 0.51 mm |
| XIV | 1.79 mg | 75.50 | 42.05 | 17.10 | 0.60 mm |
|  | 1.79 mg | 36.57 | 25.85 | 16.95 | 0.62 mm |
| XV | 1.79 mg | 95.68 | 14.63 | 7.87 | 0.72 mm |
|  | 1.72 mg | 64.47 | 91.01 | 11.86 | 0.63 mm |
| XVI | 1.82 mg | 142.92 | 102.18 | 21.83 | 0.74 mm |
|  | 1.74 mg | 167.18 | 112.07 | 13.10 | 0.70 mm |
| XVII | 1.73 mg | 5.96 | 4.48 | 8.30 | 0.63 mm |
|  | 1.99 mg | 16.26 | 3.71 | 19.14 | 0.55 mm |
| Control | 0.67 mg | 10.60 | 7.16 | 8.17 | 0.52 mm |
|  | 0.67 mg | 0.86 | 2.32 | 5.11 | 0.66 mm |

Evaluation F

Study 1892

The receptor vehicle for this evaluation was an aqueous 60% PEG400 solution, and sampling was conducted after 24 hours. The skin donors were white males.

| Formulation | Amount Applied | Amount Released (μg) | Amount in Skin (μg) | Skin Thickness |
|---|---|---|---|---|
| XIV | 82.1 mg | 28.76 | 14.57 | 0.36 mm |
| (Skin 1) | 95.8 mg | NS | 10.44 | 0.50 mm |
|  | 95.3 mg | NS | 9.65 | 0.31 mm |
| XVI | 95.2 mg | NS | 9.75 | 0.42 mm |
| (Skin-1) | 111.4 mg | 1.37 | 7.36 | 0.39 mm |
|  | 97.3 mg | ND | 6.32 | 0.43 mm |
| Control | 77.8 mg | ND | 8.12 | 0.43 mm |
| (Skin-1) | 77.4 mg | NS | 2.41 | 0.50 mm |
|  | 76.5 mg | NS | 5.50 | 0.48 mm |
| XIV | 80.9 mg | ND | 13.90 | 0.49 mm |
| (Skin-2) | 114.9 mg | ND | 10.81 | 0.49 mm |
|  | 105.8 mg | ND | 9.15 | 0.525 mm |
| XVI | 95.4 mg | ND | 6.61 | 0.52 mm |
| (Skin-2) | 97.6 mg | NS | 8.71 | 0.61 mm |
|  | 91.5 mg | NS | 17.61 | 0.54 mm |
| Control | 74.3 mg | ND | 2.92 | 0.64 mm |
| (Skin-2) | 82.6 mg | NS | 5.33 | 0.65 mm |
|  | 81.9 mg | NS | 3.64 | 0.61 mm |

NS => Not significant
ND => Not detected

Summary of Results

| Formulation | Evaluation D (72 hrs) Skin-1 | Evaluation E (24 hrs) Skin-1 | Evaluation E (24 hrs) Skin-2 |
|---|---|---|---|
| XIV | 15.18 ± 3.19 | 11.55 ± 2.64 | 11.29 ± 2.41 |
| XVI | 71.71 ± 4.39 | 7.81 ± 1.76 | 10.98 ± 5.84 |
| Control | 8.00 ± 2.81 | 5.34 ± 2.86 | 3.96 ± 1.24 |

The results illustrate an increased penetration of AG85 in skin, as compared to the control formulation.

Evaluation G

Study 2492

The receptor vehicle for this evaluation was an aqueous 60% PEG400 solution, and sampling was conducted after 24 hours. The skin donor was a white male.

| Formulation | Amount Applied | Amount Released | Amount in Skin | Skin Thickness | Cell Number | μg/mg Skin |
|---|---|---|---|---|---|---|
| Control | 126 μg | 0.0 μg | 0.87 μg | 0.34 mm | 1 | 2.59 |
|  | 121 μg | 0.0 μg | 1.39 μg | 0.40 mm | 2 | 3.48 |
|  | 136 μg | 0.0 μg | 1.85 μg | 0.60 mm | 3 | 3.07 |
| XVIII | 3.04 mg | 0.0 μg | 5.42 μg | 0.52 mm | 4 | 10.42 |
|  | 2.05 mg | 0.0 μg | 1.86 μg | 0.46 mm | 5 | 4.04 |
|  | 2.01 mg | 0.0 μg | 3.42 μg | 0.42 mm | 6 | 8.14 |
| XIX | 2.49 mg | 0.0 μg | 5.25 μg | 0.54 |  7 | 9.72 |
|  | 1.81 mg | 0.0 μg | 4.32 μg | 0.52 mm | 8 | 8.31 |
|  | 1.88 mg | 1.19 μg | 3.02 μg | 0.44 mm | 9 | 6.86 |
| XX | 2.69 mg | 0.85 μg | 3.70 μg | 0.53 mm | 11 | 6.98 |
|  | 1.76 mg | 0.0 μg | 2.23 μg | 0.59 mm | 12 | 3.78 |
|  | 3.13 mg | 0.0 μg | 3.35 μg | 0.61 mm | 13 | 5.49 |
| X | 2.25 mg | 2.52 μg | 1.11 μg | 0.47 mm | 14 | 2.36 |
|  | 1.88 mg | 0.0 μg | 1.58 μg | 0.61 mm | 15 | 2.59 |
|  | 2.60 mg | 0.0 μg | 2.70 μg | 0.52 mm | 16 | 5.19 |
| XI | 1.74 mg | 0.0 μg | 0.73 μg | 0.34 mm | 17 | 2.15 |
|  | 1.59 mg | 0.0 μg | 2.64 μg | 0.55 mm | 18 | 4.80 |
|  | 1.54 mg | 0.0 μg | 0.99 μg | 0.52 mm | 19 | 1.90 |

Evaluation H

Study 2592

The receptor vehicle for this evaluation was an aqueous 60% PEG400 solution, and sampling was conducted after 24 hours. The skin donor was a white male.

| Formulation | Amount Applied | Amount Released | Amount in Skin | Skin Thickness | Cell Number | μg/mg Skin |
|---|---|---|---|---|---|---|
| Control | 118 μg | 0.0 μg | 1.60 μg | 0.58 mm | 1 | 2.76 |
|  | 129 μg | 0.0 μg | 1.85 μg | 0.61 mm | 2 | 3.03 |
|  | 127 μg | 0.0 μg | 1.69 μg | 0.54 mm | 3 | 3.13 |
| XXI | 2.03 mg | 0.0 μg | 2.16 μg | 0.64 mm | 4 | 3.38 |
|  | 2.64 mg | 0.0 μg | 3.29 μg | 0.59 mm | 5 | 5.57 |
|  | 1.38 mg | 0.6 μg | 1.58 μg | 0.58 mm | 6 | 2.72 |
| XXII | 2.21 mg | 0.0 μg | 3.64 μg | 0.60 mm | 7 | 6.07 |
|  | 2.28 mg | 0.38 μg | 2.57 μg | 0.65 mm | 8 | 3.95 |
|  | 2.26 mg | 0.0 μg | 2.21 μg | 0.61 mm | 9 | 3.62 |
| XXIII | 2.09 mg | 0.0 μg | 1.86 μg | 0.61 mm | 11 | 3.05 |
|  | 2.08 mg | 0.0 μg | 1.14 μg | 0.50 mm | 12 | 2.28 |

-continued

| Formulation | Amount Applied | Amount Released | Amount in Skin | Skin Thickness | Cell Number | μg/mg Skin |
|---|---|---|---|---|---|---|
|  | 1.84 mm | 0.0 μg | 1.57 μg | 0.60 mm | 13 | 2.62 |
| XXIV | 0.99 mg | 0.0 μg | 2.53 μg | 0.52 mm | 14 | 4.87 |
|  | 1.10 mg | 0.09 μg | 1.46 μg | 0.58 mm | 15 | 2.52 |
|  | 0.93 mg | 0.74 μg | 1.29 μg | 0.57 mm | 16 | 2.26 |
| XII | 1.73 mg | 0.0 μg | 1.95 μg | 0.59 mm | 17 | 3.31 |
|  | 1.93 mg | 0.0 μg | 1.62 μg | 0.64 mm | 18 | 2.53 |
|  | 1.51 mg | 0.0 μg | 1.43 μg | 0.51 mm | 19 | 2.80 |

Evaluation I

Study 2592

The receptor vehicle for this evaluation was an aqueous 60% PEG400 solution, and sampling was conducted after 24 hours. The skin donors as follows: A was a white male; and B was a white male.

| Formulation | Amount Applied | Amount Released | Amount in skin | Skin Thickness | Cell No. | μg/mg skin |
|---|---|---|---|---|---|---|
| XXV | 1.18 mg | 9.34 μg | 8.48 μg | 0.40 A | 1 | 21.20 |
|  | 1.13 mg | 13.30 μg | 6.82 μg | 0.50 A | 2 | 13.64 |
|  | 0.98 mg | 5.67 μg | 5.21 μg | 0.40 A | 3 | 13.03 |
| XXVI | 1.24 mg | 33.38 μg | 15.37 μg | 0.54 A | 4 | 28.46 |
|  | 1.17 mg | 11.62 μg | 12.06 μg | 0.43 A | 5 | 28.05 |
|  | 1.35 mg | 24.68 μg | 7.31 μg | 0.53 A | 6 | 13.79 |
| XXVI | 1.73 mg | 1.02 μg | 4.84 μg | 0.44 B | 7 | 11.00 |
|  | 1.76 mg | 7.51 μg | 6.82 μg | 0.40 B | 8 | 17.05 |
|  | 1.30 mg | 25.92 μg | 4.62 μg | 0.40 B | 9 | 11.55 |
| XXV | 1.29 mg | 1.00 μg | 3.73 μg | 0.34 B | 11 | 10.97 |
|  | 1.43 mg | 1.67 μg | 3.63 μg | 0.35 B | 12 | 10.37 |
|  | 1.39 mg | 0.75 μg | 4.39 μg | 0.44 B | 13 | 9.98 |
| XXV | 1.77 mg | 4.20 μg | 4.23 μg | 0.32 B | 14 | 13.21* |
| XXVII | 1.75 mg | 27.59 μg | 9.24 μg | 0.37 B | 15 | 24.97* |
|  | 1.68 mg | 2.75 μg | 6.29 μg | 0.42 B | 16 | 14.98* |
|  | 1.57 mg | 7.69 μg | 2.41 μg | 0.38 B | 17 | 6.34 |
|  | 1.18 mg | 1.24 μg | 5.50 μg | 0.43 B | 18 | 12.79 |
|  | 0.96 mg | 0.18 μg | 1.96 μg | 0.48 B | 19 | 4.08 |

Average Amount of AG-85 in Skin (μg/mg)

| Formulation XXV | Formulation XXVI | Formulation XXVII |
|---|---|---|
| 334.52A | 334.52B | 334.52C |

| | | |
|---|---|---|
| Skin A | 15.96 | 23.43 | — |
| B | 10.44 | 13.20 | 7.74 |
| C | 17.72* (rubbed) | | |

*Product rubbed lightly into skin with spatula

Evaluation J

Study 3092

The receptor vehicle for this evaluation was an aqueous 60% PEG400 solution, and sampling was conducted after 24 hours. The skin donor for cells 1-3 and 11-19 was a white male, and the skin donor for cells 4-9 was a different white male. The results illustrate that a 1.25% AG85 anhydrous cream formulation delivered two to three times the amount of AG85 into the skin as compared to the control. When the cream formulation was occluded or rubbed in and occluded, the delivery into the skin was approximately five times that of the control formulation. Further, the amount of AG85 released into the receptor solution was much greater than the control.

| Formulation | Amount Applied | Amount Released | Amount in skin | Skin Thickness | Cell No. | μg/mg skin |
|---|---|---|---|---|---|---|
| Control | 119.00 μg | 0.45 μg | 5.12 μg | 0.63 mm | 1 | 8.13 |
|  | 129.00 μg | 0.86 μg | 4.85 μg | 0.42 mm | 2 | 11.54 |
|  | 120.00 μg | 0.43 μg | 2.60 μg | 0.55 mm | 3 | 4.73 |
| Control | 128.00 μg | 25.30 μg | 3.57 μg | 0.41 mm | 4 | 8.71 |
|  | 122.00 μg | 1.32 μg | 1.73 μg | 0.47 mm | 5 | 3.68 |
|  | 122.00 μg | 7.01 μg | 3.11 μg | 0.43 mm | 6 | 7.23 |
| XXVIII | 2.40 mg | 0.45 μg | 6.62 μg | 0.52 mm | 7 | 12.73 |
|  | 2.49 mg | 0.55 μg | 10.63 μg | 0.46 mm | 8 | 23.11 |
|  | 2.31 mg | ND | 7.88 μg | 0.44 mm | 9 | 17.91 |
| XXVIII | 2.57 mg | 57.34 μg | 12.95 μg | 0.58 mm | 11 | 22.33 |
|  | 2.36 mg | 0.87 μg | 6.18 μg | 0.65 mm | 12 | 9.51 |
|  | 2.13 mg | 70.09 μg | 6.86 μg | 0.64 mm | 13 | 10.72 |
| XXVIII | 1.96 mg | 87.88 μg | 27.31 μg | 0.45 mm | 14 | 60.69 |
|  | 1.56 mg | 53.84 μg | 17.55 μg | 0.54 mm | 15 | 32.50 |
|  | 1.81 mg | 120.68 μg | 22.99 μg | 0.64 mm | 16 | 35.92 |
| XXVIII | 1.60 mg | 78.53 μg | 32.53 μg | 0.63 mm | 17 | 51.63 |
|  | 1.81 mg | 7.59 μg | 19.85 μg | 0.53 mm | 18 | 37.45 |
|  | 1.52 mg | 103.72 μg | 17.33 μg | 0.45 mm | 19 | 38.51 |

ND => None detected
* => Top of Franz cell occluded
** => Product rubbed into skin lightly with spatula, and top of Franz occluded Evaluation K Study 3192

The receptor vehicle for this evaluation was an aqueous 60% PEG400 solution, and sampling was conducted after 24 hours. The skin donor for cells 1-13 and 17-19 was a white male, and the skin donor for cells 14-16 was a different white male.

| Formulation | Amount Applied | Amount Released | Amount in skin | Skin Thickness | Cell No. | μg/mg skin |
|---|---|---|---|---|---|---|
| Control | 144 μg | 0.79 μg | 4.88 μg | 0.37 mm | 1 | 13.1 |
|  | 131 μg | 0.84 μg | 1.83 μg | 0.26 mm | 2 | 7.0 |
|  | 148 μg | 0.0 μg | 2.59 μg | 0.42 mm | 3 | 6.1 |
| XXX | 1.10 μg | 0.0 μg | 1.55 μg | 0.54 mm | 4 | 2.8 |
|  | 0.94 μg | 0.34 μg | 0.94 μg | 0.34 mm | 5 | 2.7 |
|  | 0.82 μg | 0.62 μg | 1.50 μg | 0.64 mm | 6 | 2.3 |
| XXX | 1.17 mg | 149.64 μg | 2.56 μg | 0.37 mm | 7 | 6.9 |
|  | 1.16 mg | 21.34 μg | 1.65 μg | 0.39 mm | 8 | 4.2 |
|  | 0.87 mg | 0.50 μg | 1.69 μg | 0.50 mm | 9 | 3.3 |
| XXX | 1.16 mg | 60.29 μg | 2.07 μg | 0.55 mm | 11 | 3.7 |
|  | 1.31 mg | 2.15 μg | 1.53 μg | 0.46 mm | 12 | 3.3 |
|  | 0.90 mg | 0.31 μg | 1.31 μg | 0.77 mm | 13 | 1.7 |
| XXX | 0.75 mg | 0.36 μg | 1.15 μg | 0.52 mm | 14 | 2.2 |
|  | 1.02 mg | 0.0 μg | 1.67 μg | 0.48 mm | 15 | 3.4 |
|  | 0.89 mg | 0.0 μg | 2.19 μg | 0.53 mm | 16 | 4.1 |
| XXVIII | 1.48 mg | 0.49 μg | 4.75 μg | 0.32 mm | 17 | 14.8 |
|  | 1.86 mg | 0.0 μg | 8.40 μg | 0.31 mm | 18 | 27.1 |
|  | 1.50 mg | 3.32 μg | 5.34 μg | 0.55 mm | 19 | 9.7 |

\# => Possible hole observed in skin at completion of study
\* => Top of Franz cell occluded
\*\* => Product rubbed into skin lightly with spatula and top of Franz cell occluded

Evaluation L

Study 3292

The receptor vehicle for this evaluation was an aqueous 60% PEG400 solution, and sampling was conducted after 24 hours. The skin donor for this evaluation was a white male.

| Formulation | Amount Applied | Amount Released | Amount in skin | Skin Thickness | Cell No. | μg/mg skin |
|---|---|---|---|---|---|---|
| XXX | 0.92 mg | 1.96 μg | 3.66 μg | 0.43 mm | 4r | 8.51 |
|  | 1.00 mg | 0.0 μg | 2.73 μg | 0.37 mm | 5r | 7.38 |
|  | 1.36 mg | 0.98 μg | 2.44 μg | 0.47 mm | 6r | 5.19 |
| XXXI | 1.83 mg | 13.09 μg | 8.54 μg | 0.36 mm | 7 | 23.72 |
|  | 1.34 mg | 11.35 μg | 6.85 μg | 0.38 mm | 8 | 18.03 |
|  | 1.32 mg | Negl | 4.48 μg | 0.39 mm | 9 | 11.49 |
| XXXI | 1.27 mg | 19.50 μg | 3.26 μg | 0.37 mm | 11r | 8.81 |
|  | 1.48 mg | 31.52 μg | 7.46 μg | 0.46 mm | 12r | 16.22 |
|  | 1.33 mg | 5.31 μg | 3.09 μg | 0.38 mm | 13 | 8.13 |
| XXVIII | 2.31 mg | 56.80 μg | 13.19 μg | 0.37 mm | 14 | 35.65 |
|  | 2.07 mg | 102.55 μg | 11.00 μg | 0.36 mm | 15 | 30.56 |
|  | 2.56 mg | 2.15 μg | 7.28 μg | 0.42 mm | 16 | 17.33 |
| XXVIII | 2.23 mg | 56.62 μg | 8.72 μg | 0.42 mm | 17r | 20.76 |
|  | 1.63 mg | 14.52 μg | 6.23 μg | 0.33 mm | 18r | 18.88 |
|  | 2.62 mg | 13.02 μg | 6.23 μg | 0.44 mm | 19r | 14.16 |

\* => Hole observed in skin at completion of study
\*\* => Possible hole observed in skin at completion of study
r => Product rubbed into skin lightly with spatula and top of Franz cell occluded
Negl => Negligible amount

EXAMPLE 10

Skin penetration tests also were carried out to examine the effectiveness of Formulation XXVIII, which was a 1.25 % AG85 formulation, by administering this formulation to rats. The tests were carried out as follows. After a brief acclamation period, a group of 8 male rats (male, Sprague-Dawley, 225-250 gms) were treated with similar dermal doses of $^{14}$C-AG85, a radioactive form of Formulation XXVIII. The dose was applied over an area of 10 cm$^2$ of shaved skin. Following treatment, each rat was placed in a metabolism cage which allowed for separate collection of urine and feces. Two groups of four rats each were exposed to $^{14}$C-AG85 for 2 hours and for 24 hours, and disposition of $^{14}$C for each rat was followed. At the end of the exposure period, the unabsorbed $^{14}$C-AG85 was washed from the skin with a mild detergent solution. The rats were then euthanized shortly after the washing procedure, and the disposition of $^{14}$C was completed. After sacrifice of the rats, the liver, the kidney, the heart, a sample of fat, a sample of blood (15 mL), and skin samples from the application and surrounding sites were taken for $^{14}$C measurement. Similar tests were conducted using a control solution of 0.1 % AG85 in a PG/ETOH solution.

The results indicated that the total amount of AG85 in skin sample taken from rats treated with the 1.25% AG85 cream formulation for 24 hours averaged ten times that found in skin samples taken from rats treated with the control. These results were similar to in vitro studies conducted on human cadaverous skin.

While the invention has been described in detail and with reference to specific embodiments thereof, it will be apparent to one skilled in the art that various changes and modifications can be made without departing from the spirit and scope of the invention. Thus, it is intended that the present invention cover modifications and variations, provided that they come within the scope of the appended claims and their equivalents.

We claim:

1. A method of making an anhydrous formulation, comprising the steps of:
   (a) preparing an anhydrous hydrophilic phase comprising least one hydrophilic vehicle suitable for solubilizing at least one lipophilic, pharmaceutically active agent for administering to a host in need of treatment;
(b) preparing an oily phase comprising at least one oily component which is partially miscible with said at least one hydrophilic vehicle; and
(c) combining said oily phase with said anhydrous hydrophilic phase to form said anhydrous formulation.

2. The method of making an anhydrous formulation according to claim 1, wherein step (a) is carried out at a temperature of from about 25° C. to about 100° C.

3. The method of making an anhydrous formulation according to claim 1, wherein step (b) is carried out at a temperature of from about 25° C. to about 75° C.

4. The method of making an anhydrous formulation according to claim 1, wherein step (c) is carried out at a temperature of from about 25° C. to about 100° C.

* * * * *